United States Patent [19]

Koyama et al.

[11] Patent Number: 4,839,389

[45] Date of Patent: Jun. 13, 1989

[54] POLYPRENYL ALCOHOL-CONTAINING INJECTIONS

[75] Inventors: Noritoshi Koyama; Takayuki Ikeuchi, both of Saitama; Seiichi Araki, Gifu; Kyosuke Kitoh, Ibaraki; Katsumi Ida, Saitama, all of Japan

[73] Assignee: Eisai Co., Ltd., Tokyo, Japan

[21] Appl. No.: 6,083

[22] Filed: Jan. 23, 1987

[30] Foreign Application Priority Data

Jan. 23, 1986 [JP] Japan .................................. 61-11085

[51] Int. Cl.⁴ .................. A61K 31/045; A61K 31/685
[52] U.S. Cl. ...................................... 514/724; 514/78; 514/946
[58] Field of Search .................................. 514/78, 724

[56] References Cited

U.S. PATENT DOCUMENTS 4,599,328  7/1986  Yamatsu et al. .................... 514/134
4,624,966  11/1986  Yamamoto et al. ................ 514/724

Primary Examiner—Douglas W. Robinson
Assistant Examiner—R. Kearse
Attorney, Agent, or Firm—Wenderoth, Lind & Ponack

[57] ABSTRACT

Polyprenyl alcohol-containing injections comprising polyprenyl alcohols shown by the formula:

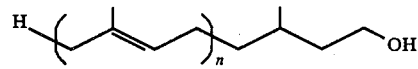

wherein n is an integer of 5 to 7, and lecithin as essential ingredients. The subject injections can enhance utilization of the polyprenyl alcohols contained therein in vivo, thereby effectively preventing or treating infectious diseases in humans or animals.

1 Claim, No Drawings

POLYPRENYL ALCOHOL-CONTAINING INJECTIONS

FIELD OF THE INVENTION

The present invention relates to polyprenyl alcohol-containing injections. More particularly, the present invention relates to polyprenyl alcohol-containing injections which aim at enhancing utilization of polyprenyl alcohol in vivo.

BACKGROUND OF THE INVENTION

Brief Description of the Prior Art

Polyprenyl alcohols shown by the formula:

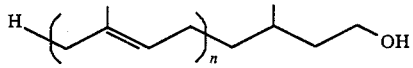

wherein n is an integer of 5 to 7, act to prevent and treat diseases caused by human or animal immunodeficiency and are particularly effective against infectious diseases of human or animals. The polyprenyl alcohols are already known in Published Unexamined Japanese Pat. App. No. 58-206517. The polyprenyl alcohols are generally administered in the form of injections.

The present inventors have made investigations for purposes of enhancing utilization of the polyprenyl alcohols in vivo in case that they are administered in the form of injections. As a result, the inventors have found that this object has been achieved when the alcohols were administered together with lecithin, and thus accomplished the present invention.

SUMMARY OF THE INVENTION

That is, an object of the present invention is to enhance utilization of the polyprenyl alcohols in accordance with the present invention in vivo. For this purpose, the present invention provides polyprenyl alcohol-containing injections comprising polyprenyl alcohols shown by the formula:

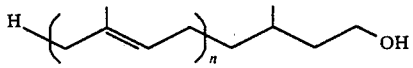

wherein n is an integer of 5 to 7, and lecithin as essential ingredients.

DETAILED DESCRIPTION OF THE PREFERRED EMBODIMENTS

In the field of medical preparations, a technique in which lecithin is incorporated in the preparation to effectively exhibit actions of drugs has been hitherto known, as shown in, for example, Published Unexamined Japanese Pat. App. Nos. 56-135416, 58-150508, 55-47608 and 57-75916. However, it is unknown that utilization of the polyprenyl alcohols in vivo could be markedly improved by incorporating lecithin in the polyprenyl alcohol.

Hereafter the present invention will be described in detail.

In the present invention, the polyprenyl alcohols are shown by the formula:

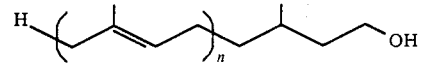

wherein n is an integer of 5 to 7. Specific examples of the polyprenyl alcohols include Compounds A, B and C described below Compound A:

3,7,11,15,19,23-Hexamethyl-6,10,14,18,22-tetracosapentaen-1-ol

Compound B:

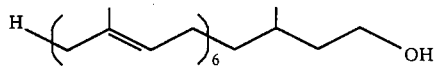

3,7,11,15,19,23,27-Heptamethyl-6,10,14,18,22,26-octacosahexaen-1-ol

Compound C:

3,7,11,15,19,23,27,31-Octamethyl-6,10,14,18,22,26,30-dotriacontaheptaen-1-ol

Lecithin in accordance with the present invention is extracted from egg yolk, soybean, etc., if necessary, further purified phospholipid-containing materials or hydrogenated products thereof or synthetic glycerophosphates, etc. can also be used.

The injection of the present invention can be administered in any form of subcutaneous, intramuscular and intravenous injections. The injection of the present invention can be prepared in a conventional manner of producing injections. While there is no particular limitation on the amounts of the polyprenyl alcohol and lecithin in the injection of the present invention, it is preferred that the polyprenyl alcohol content and the lecithin content be in the ranges of 0.01 to 10% (w/w) and 0.01 to 10% (w/w), respectively.

The present invention will be concretely described with reference to the examples described below.

EXAMPLE 1

3,7,11,15,19,23-Hexamethyl-6,10,14,18,22-tetracosapentaen-1-ol (Compound A, 1.0 g), 1.5 g of soybean lecithin, 0.7 g of sesame oil, 5.0 g of D-sorbitol and 5.0 g of propylene glycol were mixed with heating and distilled water was added to the mixture to make the volume 100 ml. After the mixture was treated with ultrasonic wave and filtered, the fitrate was filled in an ampoule. The air in the ampoule was replaced by $N_2$ gas. The ampoule was sealed and sterilized by heating to make an injection.

EXAMPLE 2

An injection was prepared in a manner similar to Example 1 except that 3,7,11,15,19,23,27-pentamethyl-6,10,14,18,22,26-octacosahexaen-1-ol (Compound B) was used in lieu of Compound A in Example 1.

EXAMPLE 3

An injection was prepared in a manner similar to Example 1 except that 3,7,11,15,19,23,27,31-octamethyl-6,10,14,18,22,26,30-dotriacontaheptaen-1-ol (Compound C) was used in lieu of Compound A in Example 1.

The effect of the present invention is explained with reference to the following experiments.

Experiment 1

Sample and Method:

Injections obtained in Examples 1 to 3 were used as samples. Each injection was intramuscularly administered to ICR male mice (6 to 7 week age, weighing 22 to 30 g) at a dose described in Table 1. After 24 hours, $2.8 \times 10^8$ CFU/mouse of clinically derived *Escherichia coli* was subcutaneously inoculated. The survival rate was determined from the number of living mice 7 days after infection. Separately, injections were prepared as in Examples 1 to 3 except that HCO-60 was used instead of soybean lecithin in Examples 1 to 3. The injections were used as comparison samples. With respect to the comparison samples, survival rates were determined in a manner similar to the above samples.

Results:

The results are shown in Table 1, in which numerical values within parenthesis show the number of living mice/the number of mice tested.

TABLE 1

| Polyprenyl Alcohol | Sample Dose | | | Comparison Sample Dose | | |
|---|---|---|---|---|---|---|
| | 25 mg/kg | 50 mg/kg | 100 mg/kg | 25 mg/kg | 50 mg/kg | 100 mg/kg |
| Compound A | 30% ($\frac{3}{10}$) | 30% ($\frac{3}{10}$) | 90% ($\frac{9}{10}$) | 0% ($\frac{0}{10}$) | 0% ($\frac{0}{10}$) | 0% ($\frac{0}{10}$) |
| Compound B | 50% ($\frac{5}{10}$) | 60% ($\frac{6}{10}$) | 100% ($\frac{10}{10}$) | 0% ($\frac{0}{10}$) | 0% ($\frac{0}{10}$) | 0% ($\frac{0}{10}$) |
| Compound C | 30% ($\frac{3}{10}$) | 50% ($\frac{5}{10}$) | 90% ($\frac{9}{10}$) | 0% ($\frac{0}{10}$) | 0% ($\frac{0}{10}$) | 0% ($\frac{0}{10}$) |

From the results of Table 1, it is noted that the injection of the present invention enhances utilization of polyprenyl alcohol in vivo.

Experiment 2

Sample and Method:

The sample and the comparison sample obtained using Compound B were chosen from the samples used in Experiment 1 and intravenously injected to ICR mice (6 week age, weighing 20 to 30 g), respectively. After 24 hours, $1.2 \times 10^7$ CFU/mouse of *Escherichia coli* was subcutaneously inoculated. Each survival rate was determined from the number of living mice 7 days after infection.

Results:

The results are shown in Table 2, in which numerical values within parenthesis shows the number of living mice/the number of mice tested.

TABLE 2

| Polyprenyl Alcohol | Sample Dose | | | Comparison Sample Dose | | |
|---|---|---|---|---|---|---|
| | 100 mg/kg | 200 mg/kg | 400 mg/kg | 100 mg/kg | 200 mg/kg | 400 mg/kg |
| Compound B | 0% ($\frac{0}{10}$) | 40% ($\frac{4}{10}$) | 90% ($\frac{9}{10}$) | 0% ($\frac{0}{10}$) | 20% ($\frac{2}{10}$) | 60% ($\frac{6}{10}$) |

From the results, a conclusion similar to that in Experiment 1 is noted.

Experiment 3

Sample and Method:

An injection was prepared in a manner similar to Example 2 except that egg yolk lecithin was used instead of soybean lecithin in Example 2. The injection was used as a sample. The injection was intramuscularly administered to ICR mice (6 week age, weighing 30 g). After 24 hours, $6.9 \times 10^7$ CFU/mouse of clinically derived *Escherichia coli* was subcutaneously inoculated. The survival rate was determined from the number of living mice 7 days after infection.

Results:

The results are shown in Table 3, in which numerical values within parenthesis show the number of living mice/the number of mice tested.

TABLE 3

| Polyprenyl Alcohol | Yolk Lecithin Dose | | |
|---|---|---|---|
| | 25 mg/kg | 50 mg/kg | 100 mg/kg |
| Compound B | 10% ($\frac{1}{10}$) | 70% ($\frac{7}{10}$) | 100% ($\frac{10}{10}$) |

From the results, a conclusion similar to that in Experiment 1 is noted.

While the invention has been described in detail and with reference to specific embodiments thereof, it will be apparent to one skilled in the art that various changes and modifications can be made therein without departing from the spirit and scope thereof.

What is claimed is:
1. A polyprenyl alcohol-containing injection preparation comprising 0.01 to 10% (w/w) of a polyprenyl alcohol of the formula:
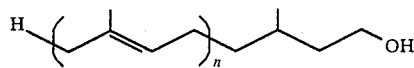
wherein n is an integer of 5 to 7, 0.01 to 10% (w/w) of lecithin, and the balance consisting essentially of water.